(12) United States Patent
Kataoka

(10) Patent No.: US 7,991,569 B2
(45) Date of Patent: Aug. 2, 2011

(54) MOBILITY NORMALIZER, NORMALIZING METHOD, NORMALIZING PROGRAM, SELF-ORGANIZED MAP, SUBSTANCE DETECTING METHOD, DETECTING PROGRAM, DETECTION RULE CREATING METHOD, AND DATA STRUCTURE

(75) Inventor: Hiromi Kataoka, Kochi (JP)

(73) Assignee: Kochi University, Kochi (JP)

( * ) Notice: Subject to any disclaimer, the term of this patent is extended or adjusted under 35 U.S.C. 154(b) by 444 days.

(21) Appl. No.: 12/084,370

(22) PCT Filed: Jul. 11, 2006

(86) PCT No.: PCT/JP2006/313759
§ 371 (c)(1),
(2), (4) Date: Apr. 30, 2008

(87) PCT Pub. No.: WO2007/058001
PCT Pub. Date: May 24, 2007

(65) Prior Publication Data
US 2009/0136139 A1     May 28, 2009

(30) Foreign Application Priority Data

Nov. 17, 2005  (JP) .................................. 2005-332835

(51) Int. Cl.
*G01R 11/02* (2006.01)
(52) U.S. Cl. ............. 702/66; 702/69; 702/182; 702/183
(58) Field of Classification Search .................... 702/30, 702/35, 63, 66, 73, 150, 176, 179; 250/282; 382/124, 129; 600/509
See application file for complete search history.

(56) References Cited

U.S. PATENT DOCUMENTS

| 6,195,449 B1 * | 2/2001 | Bogden et al. ................. 382/129 |
| 6,906,320 B2 * | 6/2005 | Sachs et al. .................... 250/282 |

(Continued)

FOREIGN PATENT DOCUMENTS

JP    A-05-312812    11/1993

(Continued)

OTHER PUBLICATIONS

International Search Report issued on Aug. 29, 2006 in connection with corresponding PCT application No. PCT/JP2006/313759 filed Jul. 11, 2006.

(Continued)

*Primary Examiner* — Michael P Nghiem
*Assistant Examiner* — Felix E Suarez
(74) *Attorney, Agent, or Firm* — Posz Law Group, PLC

(57) ABSTRACT

The object of the present invention is to provide an apparatus, a method, a program, and a self-organizing map which are capable of normalizing mobility without using a marker, as well as a substance detection method, a program, a detection rule creating method, and a data structure which use normalized mobility. The mobility normalizing method comprises the steps of determining a plurality of warping functions converting data to be corrected, which is unit time sequence data obtained by measuring mobility, to the respective plurality of reference waveform data sets, and a DTW distance associated with each warping function; evaluating a minimum value of the plurality of DTW distances, and determining the warping function associated with the determined minimum DTW distance; determining a slope and an intercept of a straight line approximating the determined warping function; and correcting the data to be corrected using a linear function specified by the slope and the intercept.

17 Claims, 10 Drawing Sheets

U.S. PATENT DOCUMENTS 7,539,532 B2 * 5/2009 Tran .............................. 600/509

FOREIGN PATENT DOCUMENTS

| JP | A-06-096138 | 4/1994 |
|---|---|---|
| JP | A-2001-074694 | 3/2001 |

OTHER PUBLICATIONS

Kataoka et al., *A Data Mining System for Protein Electrophoresis Waveforms*, Japanese Journal of Clinical Laboratory Automation, The Japan Society for Clinical Laboratory Automation, Jun. 1, 2001, vol. 26, No. 3, pp. 170-175.

Kataoka et al., *Development of a General Algorithm Normalizing Chromatography Mobility for Discovering Patterns*, Japanese Journal of Clinical Laboratory Automation, The Japan Society for Clinical Laboratory Automation, Sep. 1, 2005, vol. 30, No. 4, p. 548.

Kataoka et al., *Data Mining in the Clinical Laboratory*, Japanese Journal of Clinical Laboratory Automation, The Japan Society for Clinical Laboratory Automation, Dec. 1, 2001, vol. 26, No. 6, pp. 689-696.

Kataoka et al., RDB Expression of Decision Tree, and Knowledge Discovery Supporting System, IEICE Technical Report, The Institute of Electronics, Information, and Communication Engineers, Jul. 12, 2001, vol. 11, No. 193, pp. 105-112.

Kataoka et al., *A Similarity Wave Data Search Based on Dynamic Programming-SOM*, Transactions of Information Processing Society of Japan, Information Processing Society of Japan, Sep. 15, 2001, vol. 42, pp. 92-99.

Kataoka et al., *The Future Guaranteeing the Advanced Accuracy*, The Japanese Journal of Clinical Pathology, Japanese Society of Laboratory Medicine, Sep. 25, 1999, vol. 47, No. 9, pp. 823-829.

Hagimoto et al., *A Data Correction Scheme for Comparing Different Time Series Microarrays*, Information Processing Society of Japan Kenkyu Hokoku, Information Processing Society of Japan, Oct. 7, 2005, vol. 2005, No. 99, pp. 25-32.

* cited by examiner

```
779 <= 0.00048 :
|  399 <= 0.06172 :
|  |  445 > 0.00128 : Normal (7.0)
|  |  445 <= 0.00128 :
|  |  |  503 <= 0.00452 : Mpro (16.0)
|  |  |  503 > 0.00452 : Normal (5.0)
|  399 > 0.06172 :
|  |  449 <= 0.00133 :
|  |  |  374 <= 0.00545 : Normal (21.0)
|  |  |  374 > 0.00545 : Mpro (4.0)
|  |  449 > 0.00133 :
|  |  |  436 <= 0.00253 : Normal (551.0)
|  |  |  436 > 0.00253 :
|  |  |  |  734 <= 0.0021 : Normal (23.0)
|  |  |  |  734 > 0.0021 : Mpro (2.0)
779 > 0.00048 :
|  578 <= 0.00433 : Mpro (64.0)
|  578 > 0.00433 :
|  |  760 <= 0.00016 : Mpro (3.0)
|  |  760 > 0.00016 : Normal (2.0)
```

FIG. 15

```
674 <= 4584 :
|  684 <= 1135 :
|  |  715 > 1115 : Mpro (6.0)
|  |  715 <= 1115 :
|  |  |  639 > 1473 : Mpro (3.0)
|  |  |  639 <= 1473 :
|  |  |  |  692 <= 293 : Mpro (2.0)
|  |  |  |  692 > 293 : Normal (29.0)
|  684 > 1135 :
|  |  694 <= 5595 :
|  |  |  663 <= 3086 : Normal (1078.0/10.0)
|  |  |  663 > 3086 :
|  |  |  |  740 <= 241 : Mpro (5.0)
|  |  |  |  740 > 241 : Normal (20.0)
|  |  694 > 5595 :
|  |  |  727 <= 1281 : Mpro (6.0)
|  |  |  727 > 1281 :
|  |  |  |  459 <= 676 : Normal (34.0/1.0)
|  |  |  |  459 > 676 : Mpro (2.0)
674 > 4584 :
|  718 <= 2333 : Mpro (14.0)
|  718 > 2333 : Normal (12.0/1.0)
```

FIG. 16

```
x > 706 : Mpro (60.0)
x <= 706 :
|  y <= 0.08225 :
|  |  y <= 0.0141 :
|  |  |  x <= 482 :
|  |  |  |  y <= 0.00282 : Normal (840.0/35.0)
|  |  |  |  y > 0.00282 :
|  |  |  |  |  y > 0.00622 : Mpro (5.0)
|  |  |  |  |  y <= 0.00622 :
|  |  |  |  |  |  lhw <= 14 : Normal (11.0)
|  |  |  |  |  |  lhw > 14 :
|  |  |  |  |  |  |  rhw > 13 : Normal (3.0)
|  |  |  |  |  |  |  rhw <= 13 :
|  |  |  |  |  |  |  |  rhw <= 8 : Normal (3.0/1.0)
|  |  |  |  |  |  |  |  rhw > 8 : Mpro (3.0)

RULE CONTINUES TO A TOTAL OF 347 NODESc
```

MOBILITY NORMALIZER, NORMALIZING METHOD, NORMALIZING PROGRAM, SELF-ORGANIZED MAP, SUBSTANCE DETECTING METHOD, DETECTING PROGRAM, DETECTION RULE CREATING METHOD, AND DATA STRUCTURE

TECHNICAL FIELD

The present invention relates to mobility normalization processes, and more particularly, to a mobility normalizing apparatus, a normalizing method, a normalizing program, and a self-organizing map which are capable of correcting mobility without using a marker substance, and to a substance detection method, a detection program, a detection rule creating method, and a data structure which use the normalized mobility.

BACKGROUND ART

For analysis of waveform information obtained by electrophoresis for use in clinical examinations, gene analyses, and the like, a method of specifying the separated substance based on its mobility is employed. Since the mobility varies depending on various analytical conditions, it is then necessary to normalize the mobility. Methods for mobility normalization that have been used include a method in which a reference marker substance (hereinafter also referred to simply as a "marker") is mixed into a sample, and a method in which the mobility is corrected using, for example, a characteristic waveform peak as an index.

In the case of serum protein electrophoretic analysis, for example, a plurality of samples can be analyzed simultaneously by applying several tens of samples to one film sheet of cellulose acetate. Therefore, according to a method for correcting mobilities inside the sheet (see Non-Patent Document 1 listed below) invented by the present inventor, a monitoring sample whose mobility has been tested is mixed into analytical samples, and all of the mobilities can be corrected based on the mobility of the monitoring sample.

With regard to capillary zone electrophoresis, an estimation method using theoretical mobility is known (see Patent Document 1 listed below).

On the other hand, a method for detecting M protein (see Patent Document 2 listed below) and a method for determining pathosis (see Patent Document 3 listed below), which use feature amounts prepared from mobility measurement data, are known.

Patent Document 1: Japanese Unexamined Patent Publication No. 2001-074694
Patent Document 2: Japanese Unexamined Patent Publication No. 5-312812
Patent Document 3: Japanese Unexamined Patent Publication No. 6-96138
Non-Patent Document 1: Hiromi KATAOKA, Masahide SASAKI, Hideaki NISHIDA, Kyoko TAKEDA, and Tetsuro SUGIURA: "*Seido Hoshouno Kongono Tenkai, Rinshou Byouri* (Future Evolution of Accuracy Assurance, Clinical Pathology)", 47(9), pp. 823-829, 1999.

DISCLOSURE OF THE INVENTION

Problems to be Solved by the Invention

However, in the case of an analytical process that cannot mix a marker substance, or an analytical target that cannot produce a characteristic waveform peak, the prior art methods have been unable to correct the mobility.

In addition, in the case of an analytical process capable of analyzing only one sample in one analysis, such as capillary zone electrophoresis or liquid chromatography, methods of mixing a marker substance into a sample have been the only methods capable of correcting the mobility, and mobility correction using other analytical results has been impossible.

In actual clinical examination applications, the mobility correction method according to Patent Document 1 has been impossible to apply as a correction method based on theoretical mobility, due to various artifacts being added.

The M protein detection method according to Patent Document 2 and the pathosis determination method according to Patent Document 3 have failed to provide sufficient detection or determination accuracy.

In order to overcome the aforementioned problems, the present invention aims to provide a mobility normalizing apparatus, a normalizing method, a normalizing program, and a self-organizing map which are capable of correcting mobility, as well as a substance detection method, a detection program, a detection rule creating method, and a data structure which use the normalized mobility, for analytical processes in which correction can only be done using methods of mixing a marker substance into samples, or analytical processes in which mobility correction using a marker substance is impossible.

Means for Solving the Problems

A mobility normalizing apparatus (1) according to the present invention comprises a recording unit containing a plurality of reference waveform data sets, and a processing unit; wherein the processing unit: when externally acquired mobility measurement data is unit time sequence data, defines the measurement data as data to be corrected; when externally acquired mobility measurement data is a plurality of two-dimensional data sets associated with time information and measured values, interpolates these two-dimensional data sets to create the data to be corrected, which is unit time sequence data; reads the plurality of reference waveform data sets from the recording unit, and determines a plurality of warping functions converting the data to be corrected to the respective plurality of reference waveform data sets, and a DTW distance associated with each warping function; evaluates a minimum value of the plurality of DTW distances, and determines the warping function associated with the determined minimum DTW distance; determines a slope and an intercept of a straight line approximating the determined warping function; and corrects the data to be corrected using a linear function specified by the slope and the intercept.

In a mobility normalizing apparatus (2) according to the mobility normalizing apparatus (1), the processing unit calculates a slope between given vertices for each determined warping function, excludes slopes included in predetermined areas at both ends when the plurality of slopes between vertices are arranged in order of increasing size, and determines the slope of the straight line approximating the warping function based on the slopes between vertices which are not excluded.

In a mobility normalizing apparatus (3) according to the mobility normalizing apparatus (2), the processing unit determines a median of the plurality of slopes between vertices as the slope of the straight line approximating the warping function.

In a mobility normalizing apparatus (4) according to the mobility normalizing apparatus (1), the plurality of reference waveform data sets are data obtained by correcting mobility measurement data for an analyte containing a marker substance, using the mobility of the marker substance.

In a mobility normalizing apparatus (5) according to the mobility normalizing apparatus (1), the plurality of reference waveform data sets are data forming a self-organizing map created using a plurality of mobility measurement data sets.

Moreover, a mobility normalizing method (1) according to the present invention comprises a first step of determining a plurality of warping functions converting data to be corrected, which is unit time sequence data obtained by measuring mobility, to respective plurality of given reference waveform data sets, and a DTW distance associated with each warping function; a second step of evaluating a minimum value of the plurality of DTW distances, and determining the warping function associated with the determined minimum DTW distance; a third step of determining a slope and an intercept of a straight line approximating the determined warping function; and a fourth step of correcting the data to be corrected using a linear function specified by the slope and the intercept.

In a mobility normalizing method (2) according to the mobility normalizing method (1), the data obtained by measuring mobility is a plurality of two-dimensional data sets associated with time information and measured values; and the data to be corrected is unit time sequence data created by interpolating the plurality of two-dimensional data sets.

In a mobility normalizing method (3) according to the mobility normalizing method (1), the third step comprises a fifth step of calculating a slope between given vertices for each warping function determined in the second step; and a sixth step of excluding slopes included in predetermined areas at both ends when the plurality of slopes between vertices are arranged in order of increasing size, and determining the slope of the straight line approximating the warping function based on the slopes between vertices which are not excluded.

In a mobility normalizing method (4) according to the mobility normalizing method (1), the sixth step is a step of determining a median of the plurality of slopes between vertices as the slope of the straight line approximating the warping function.

In a mobility normalizing method (5) according to the mobility normalizing method (1), the plurality of reference waveform data sets are data obtained by correcting mobility measurement data for an analyte containing a marker substance, using the mobility of the marker substance.

In a mobility normalizing method (6) according to the mobility normalizing method (1), the plurality of reference waveform data sets are data forming a self-organizing map created using a plurality of mobility measurement data sets.

In addition, a computer-readable recording medium (1) according to the present invention contains a mobility normalizing program, which is used in an apparatus comprising a recording unit containing a plurality of reference waveform data sets, and a processing unit, and which causes the processing unit to implement a first function of determining a plurality of warping functions converting data to be corrected, which is unit time sequence data obtained by measuring mobility, to the respective plurality of reference waveform data sets, and a DTW distance associated with each warping function; a second function of evaluating a minimum value of the plurality of DTW distances, and determining the warping function associated with the determined minimum DTW distance; a third function of determining a slope and an intercept of a straight line approximating the determined warping function; and a fourth function of correcting the data to be corrected using a linear function specified by the slope and the intercept.

Furthermore, a computer-readable recording medium (2) according to the present invention contains a self-organizing map, which is used as the reference waveform data in the mobility normalizing method (1), and which is created by a learning process executed by a computer, using waveform data obtained by visually correcting data to be corrected, which is unit time sequence data obtained by measuring mobility of an analyte, or using waveform data obtained by correcting waveform data obtained by correcting data to be corrected, which is unit time sequence data obtained by measuring mobility of an analyte containing a marker substance, based on the mobility of the marker substance.

Furthermore, a substance detection method (1) according to the present invention is a method for detecting a substance, using a decision tree determined as a detection rule by learning that uses supervised data; wherein the decision tree is determined by learning that uses normalized data obtained by correcting a plurality of mobility measurement data sets for a plurality of analytes, using the mobility normalizing method (1); and the supervised data including information representing the presence or absence of a given substance, which is associated with each measurement data set.

In a substance detection method (2) according to the substance detection method (1), the substance is M protein; and under the condition that the mobility of albumin is 400 and the mobility of dimethylformamide in the $\gamma$ region is 800, the decision tree is described in the form of combinations of mobilities and determination signs as shown in FIG. 14 or FIG. 15.

Furthermore, a computer-readable recording medium (3) according to the present invention contains a substance detection program which causes a computer to implement the function of detecting a substance, using a decision tree determined by learning that uses supervised data as a detection rule; wherein the decision tree is determined by learning that uses normalized data obtained by correcting a plurality of mobility measurement data sets for a plurality of analytes, using the mobility normalizing method (1); and the supervised data including information representing the presence or absence of a given substance, which is associated with each measurement data set.

Furthermore, a substance detection rule creating method according to the present invention is a method for creating a detection rule for use in detecting a substance, which comprises a first step of using a computer to correct a plurality of mobility measurement data sets for a plurality of analytes, using the mobility normalizing method (1), to create normalized data; and a second step of determining a decision tree as a detection rule by learning, using supervised data including information representing the presence or absence of a given substance, which is associated with each measurement data set, and the normalized data.

Furthermore, a computer-readable recording medium (4) according to the present invention contains a data structure (1), which is used as a substance detection rule, and represents a decision tree determined by learning that uses normalized data obtained by correcting a plurality of mobility measurement data sets for a plurality of analytes, using the mobility normalizing method (1); and supervised data including information representing the presence or absence of a given substance, which is associated with each measurement data set.

Furthermore, a computer-readable recording medium (5) contains a data structure (2) according to the data structure (1), wherein the substance is M protein; and, under the condition that the mobility of albumin is 400 and the mobility of dimethylformamide in the γ region is 800, the decision tree is described in the form of combinations of mobilities and determination signs as shown in FIG. 14 or FIG. 15.

Effects of the Invention

The present invention enables normalization of mobility measurement data using the waveform pattern of the mobility measurement data of an analytical target, without mixing a marker substance into a sample, thus enabling the components of an analytical target to be separated more accurately. For example, the invention is also effective in cases where mixing a marker substance into samples causes adsorption or the like of the samples onto the marker substance to hinder accurate measurement of the target substance.

In the invention, a warping function determined by Dynamic Time Warping (DTW) is linearly approximated, and each measurement data set is corrected using the slope of the warping function. This enables a correction based on the entire waveform pattern, thus enabling accurate mobility correction without being affected by some portions of irregular measurement data on the measured waveform.

In the invention, the measurement data can be corrected using the waveform patterns clustered by self-organizing map (Self Organization Map) as a reference. Therefore, the invention is also applicable to measurement data in which a characteristic waveform peak cannot be detected.

The present invention is capable of correcting measurement data on a large amount of an analyte at high speed, and is also capable of being automated.

In addition, even if an analytical process that can use a marker is applicable, mobilities can be corrected by an analytical process that does not use a marker in an examination room of a general hospital, using a self-organizing map created with waveform data analyzed in some reference examination rooms or the like. Therefore, when the marker substance is expensive, analysis can be conducted economically in an examination room of a general hospital. In this case, a self-organizing map template (reference waveform data) with higher accuracy can be created by accumulating many cases. Therefore, it is desirable that a newer self-organizing map be provided as necessary to general hospitals or the like.

For examination of a substance with which a marker cannot be used, accurate mobility correction can be performed by visually correcting only the self-organizing map template in reference examination rooms or the like.

The present invention can be applied to various analytical instruments such as an electrophoresis apparatus, a chromatograph, etc. The invention can be applied to, for example, a serum protein electrophoresis apparatus, a capillary electrophoresis apparatus, a liquid chromatograph, a gas chromatograph, an affinity chromatograph, etc.

In addition, the present invention enables accurate detection of a substance that can be analyzed based on its mobility, for example, a specific protein. The invention is particularly effective in detecting M protein.

BRIEF DESCRIPTION OF THE DRAWINGS

FIG. 15 is a diagram showing another example of an M protein detection rule for use in the substance detection method according to the present invention.

FIG. 16 is a diagram showing an M protein detection rule determined using a prior art technique.

Figure 1:
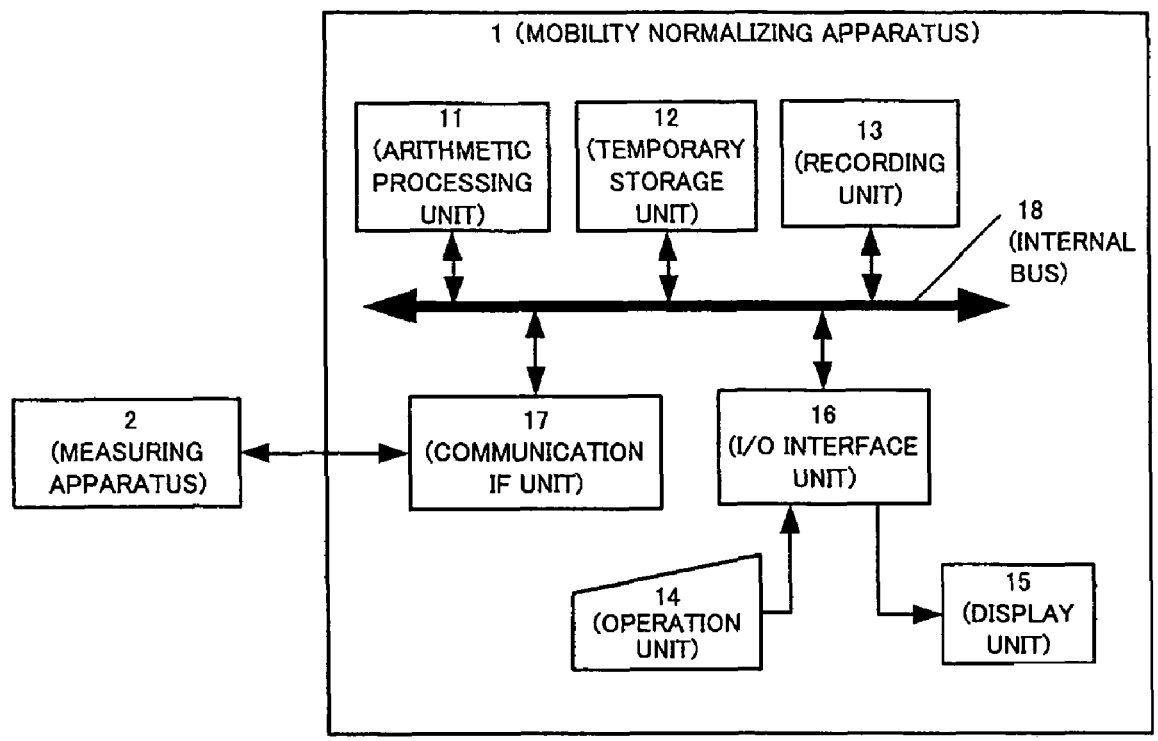
FIG. 1 is a block diagram showing the schematic configuration of a mobility normalizing apparatus according to an embodiment of the present invention.

EXPLANATION OF REFERENCE NUMERALS 1 mobility normalizing apparatus
11 arithmetic processing unit
12 temporary storage unit
13 recording unit
14 operation unit
15 display unit
16 I/O interface unit
17 communication interface unit
18 internal bus
2 measuring apparatus Best Mode for Carrying Out the Invention Embodiments of the present invention will hereinafter be described with reference to the attached drawings.

FIG. 1 is a block diagram showing the general configuration of a mobility normalizing apparatus according to an embodiment of the present invention. The normalizing apparatus 1 comprises an arithmetic processing unit 11; a temporary storage unit 12; a recording unit 13; an operation unit 14 that provides instructions or inputs data to the arithmetic processing unit 11; a display unit 15 that displays processing results from the arithmetic processing unit 11; an interface unit (hereinafter referred to as an "I/O IF unit") 16 between the operation unit 14 and the display unit 15; a communication interface unit (hereinafter referred to as a "communication IF unit") 17 that exchanges data with an external measuring apparatus 2; and an internal bus 18 for exchanging data among the internal units. The measuring apparatus 2 is a measuring apparatus capable of acquiring mobility-related data from an electrophoresis apparatus, a chromatograph, or the like.

When the normalizing apparatus 1 is constructed using, for example, a computer, the arithmetic processing unit 11, temporary storage unit 12, and recording unit 13 may be a CPU, an RAM, and a hard disk, respectively. The operation unit 14 may be a keyboard, a mouse, or a touch panel. The I/O IF unit 16 may be a serial or parallel interface compatible with the operation unit 14. The I/O IF unit 16 has a video memory or a digital-to-analog converter, and outputs an analog signal in accordance with the video format of the display unit 15, whereby an image for presenting information is displayed on the display unit 15. Where the display unit 15 has a function of a digital-to-analog conversion of video data, the I/O IF unit 16 may have a function of outputting a predetermined digital signal. The configuration of FIG. 1 may also be modified so as to use a portion of the temporary storage unit 12 as a video memory.

Figure 2:
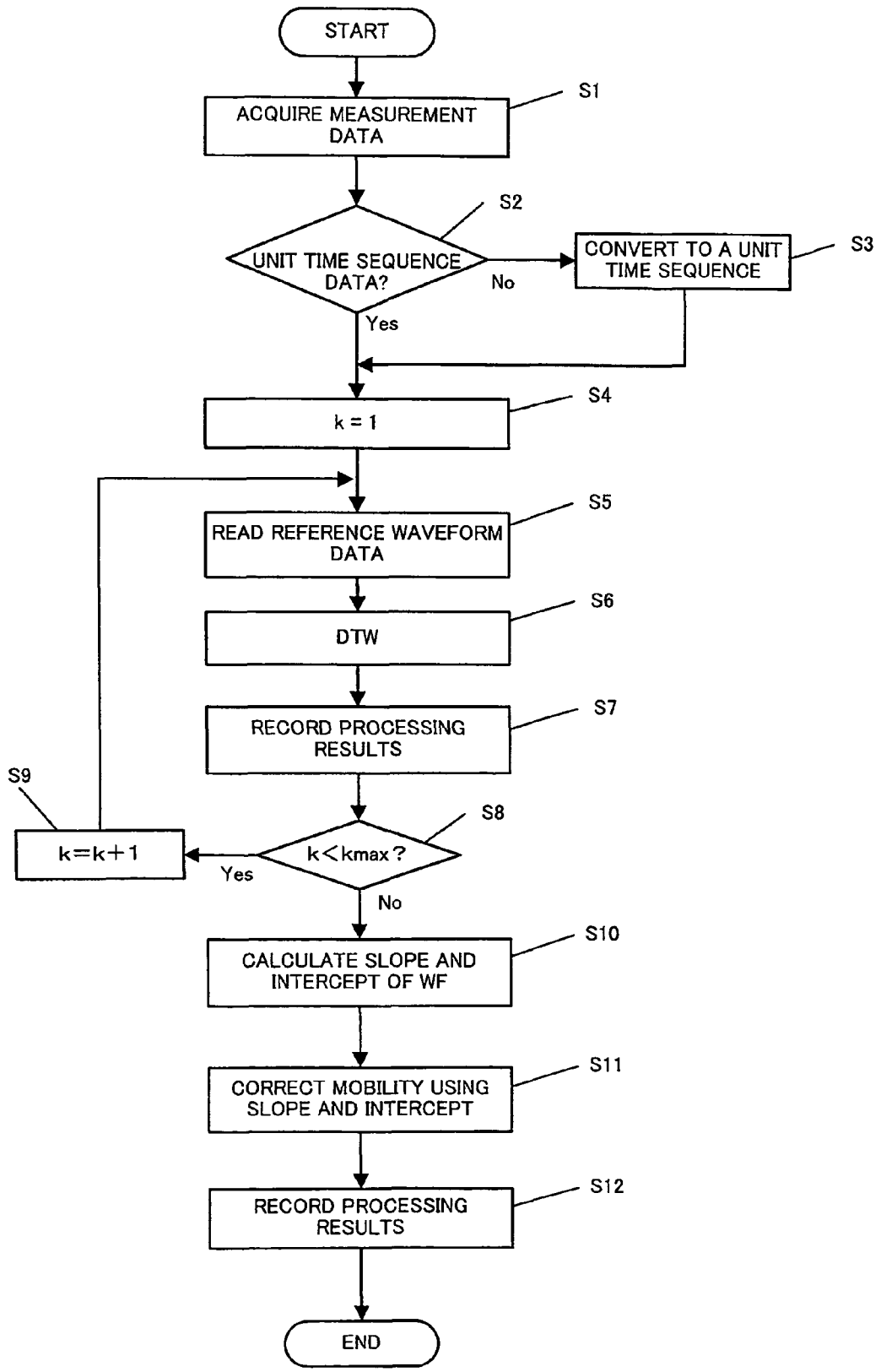
FIG. 2 is a flowchart showing the operation of a mobility normalizing apparatus according to an embodiment of the present invention.

FIG. 2 is a flowchart showing the operation of the normalizing apparatus 1 according to the embodiment. The operation of the normalizing apparatus 1 will be described in detail below with reference to FIG. 2. The following processing is explained as being performed by the arithmetic processing unit 11 of the normalizing apparatus 1, unless otherwise specified. The arithmetic processing unit 11 performs predetermined processing as follows: The arithmetic processing unit 11 acquires data inputted through an operation of the operation unit 14 and records the data in the recording unit 13. The arithmetic processing unit 11 reads the data from the recording unit 13 into the temporary storage unit 12 as required, performs predetermined processing, and subsequently records the results in the recording unit 13. The arithmetic processing unit 11 also creates screen data for encouraging the operation of the operation unit 14, screen data for displaying the processing results, etc., and displays these images on the display unit 15 via the video RAM of the I/O IF unit 16. In the recording unit 13, a plurality of reference waveform data sets for use as criteria are databased and stored in a predetermined format. As will be described below, the reference waveform data can be determined as a self-organizing map (hereinafter also referred to as an "SOM"). Targets of mobility measurement include general components of mammals, microorganisms, plants, and the like, such as blood, urine, spinal fluid, lymph, tissue fluid, culture media, and the like. Analytical targets are substances that can be analyzed based on their mobilities, such as proteins, sugars, lipids, and the like.

In Step S1, the arithmetic processing unit 11 acquires measurement data from the measuring apparatus via the communication IF unit 17 and records the data into the recording unit 13.

Figure 3:
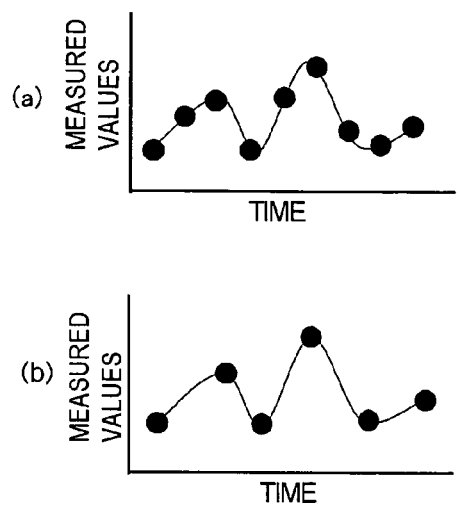
FIG. 3 (a) and FIG. 3 (b) are graphs showing unit time sequence data and differential coefficient data at changing peak points, respectively.

In Step S2, the arithmetic processing unit 11 determines whether the measurement data acquired in Step S1 is time series one-dimensional data measured at given intervals of time (hereinafter referred to as "unit time sequence data") or not. If the data is not unit time sequence data, the arithmetic processing unit 11 moves to Step S3 and creates unit time sequence data based on the acquired measurement data. In the case of an electrophoresis apparatus, for example, the measurement data outputted from the measuring apparatus is usually unit time sequence data, so that the arithmetic processing unit 11 can proceed onto the steps after Step S4, directly using the measurement data. In the case of chromatography, measurement data outputted from the measuring apparatus is usually differential coefficient data at changing peak points (a two-dimensional data sequence of peak times and peak amplitudes). Therefore, in the case of such a two-dimensional data sequence of differential coefficients at changing peak points, unit time sequence data is created based on this data sequence. FIGS. 3 (a) and (b) are graphs showing unit time sequence data and differential coefficient data at changing peak points, respectively. At this time, in order for the arithmetic processing unit 11 to make a determination in Step S2, for example, prior to or after the receipt of measurement data from the measuring apparatus, an operator may input information as to whether the measurement data received by operating the operation unit 14 is unit time sequence data or not, and record this input of information, which is associated with the measurement data, into the recording unit 13.

Steps S4 to S8 are steps of determining the reference waveform data that approximates the acquired measurement data.

In Step S4, a counter k for counting repeated processes is set to 1.

In Step S5, one waveform data set of the plurality of recorded reference waveform data sets is read from the recording unit 13.

Figure 4:
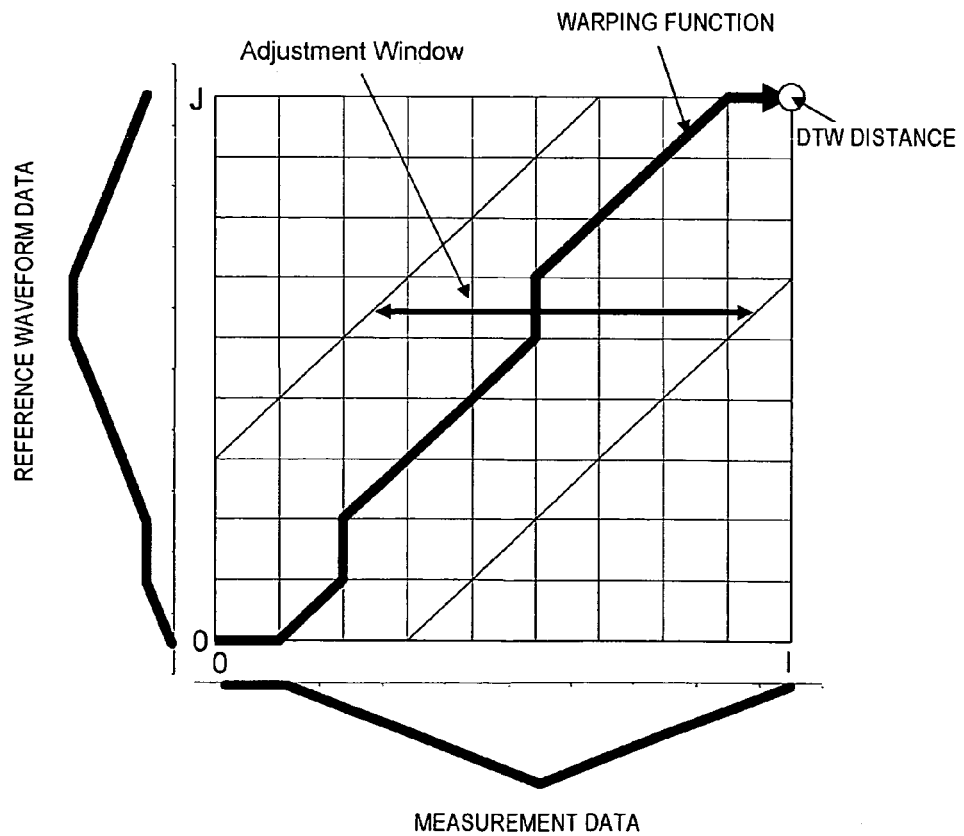
FIG. 4 is a diagram showing the concept of DTW.

In Step S6, Dynamic Time Warping (DTW) is applied to the reference waveform data read in Step S5 and the measurement data (unit time sequence data). More specifically, a warping function (hereinafter also referred to as a "WF") that converts each measurement data set to each reference waveform data set, and then a DTW distance, which is a distance along the WF, is determined. Since DTW is a well-known process, the concept of DTW is shown in FIG. 4, with a detailed explanation being omitted. In FIG. 4, positive integer values are sequentially assigned to one unit time sequence data set. The reference waveform data set is assigned 0 to J, and the measurement data set is assigned 0 to I.

In Step S7, the arithmetic processing unit 11 records the WF and the DTW distance determined in Step S6, which are associated with the reference waveform data set, into the recording unit 13. In this embodiment, as shown in FIG. 4, since the WF draws a line graph on a two-dimensional plane, the coordinates (i, j) ($0 \leq i \leq I$, $0 \leq j \leq J$) at each vertex are recorded into the recording unit 13.

In Step S8, the arithmetic processing unit 11 determines whether the value of the counter k is smaller than the total number, kmax, of the reference waveform data sets or not, thereby determining whether the processes of from Steps S5 to S7 have been completed for all of the reference waveform data sets. Where k<kmax, there still remains one or more reference waveform data sets to be processed, so that the arithmetic processing unit 11 moves to Step S9 to increase the counter k by one, and returns to Step S5. In this manner, the processes of from Steps S5 to S7 are applied to all of the reference waveform data sets.

In Step S10, the arithmetic processing unit 11 determines the minimum value of the DTW distances recorded in the recording unit 13, reads the coordinate data set of the WF associated with the minimum value from the recording unit 13, and determines the slope α (primary coefficient) and intercept β (constant term) of the linear function for linear approximation of the WF. Since the WF is theoretically a straight line, linear regression or a non-parametric linear regression method (for example, the Passing-Bablock technique) can be employed.

Figure 5:
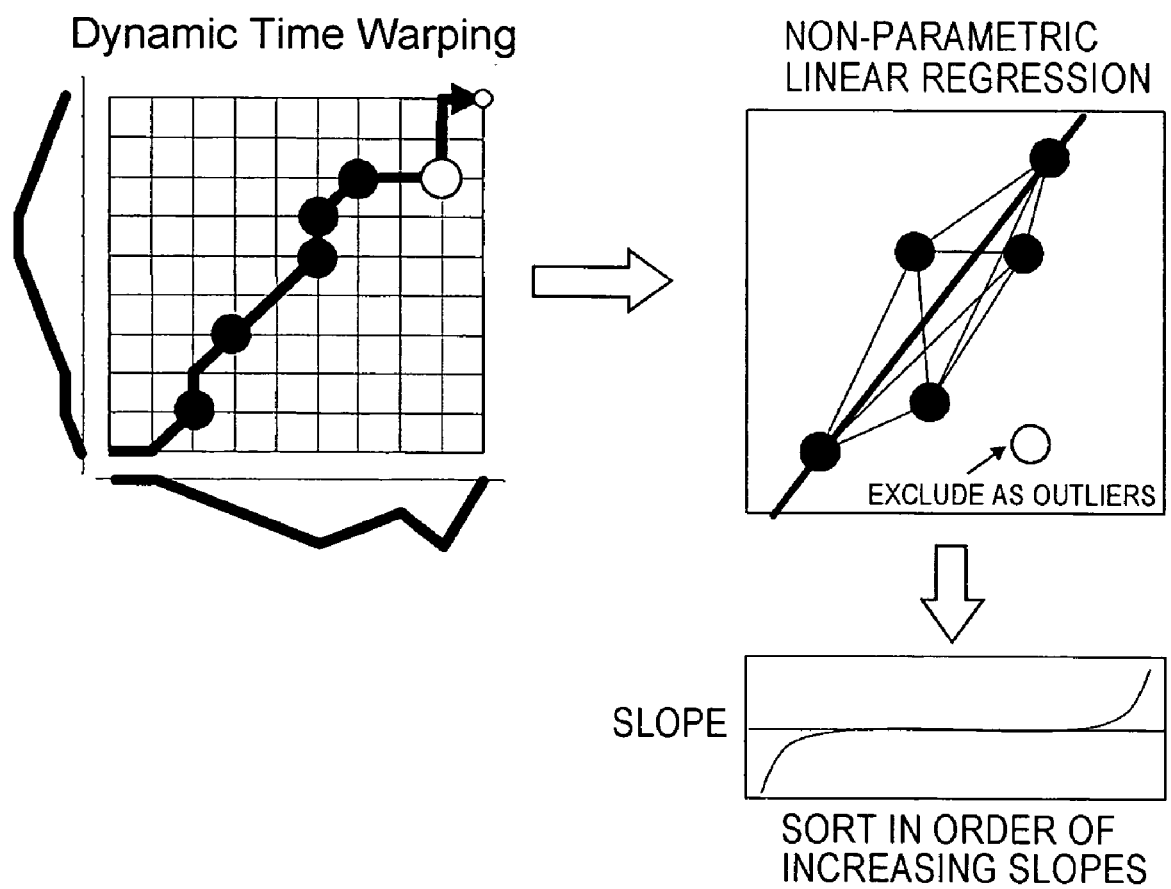
FIG. 5 is a schematic diagram showing the process of determining the slope of a WF in the normalizing method according to an embodiment of the invention.

In this embodiment, given two coordinate data sets are selected from a plurality of coordinate data sets that represent vertices of the WF read from the recording unit 13, and the slope of the straight line that passes these two points is determined. The median of all of the slopes is determined as the slope α of the straight line that approximates the WF. Similarly with respect to the intercept β, the intercepts of all of the combinations are calculated, and the median of these values is determined as the intercept β of the straight line that approximates the WF. In this manner, both the slope α and the intercept β can be determined using the same non-parametric technique. FIG. 5 is a diagram that schematically illustrates this process. The lower right partial diagram of FIG. 5 is a graph in which slopes between given coordinate data sets are arranged in ascending order from the left. Although the line of this graph is substantially flat around the center, it abruptly changes at around the right and left ends. The slopes of these areas are determined using, of the coordinate data sets that represent vertices of the WF, those of the vertices that greatly fall out of the straight line when the WF is linearly approximated. Thus, using the median of the slope distribution, outliers can be eliminated.

In Step S11, each measurement data set is corrected using the slope α and intercept β determined in Step S10. More specifically, using the value of i' determined in accordance with the equation, $i'=\alpha \times i+\beta$ (wherein $0 \leq i \leq I$), the position of the mobility m(i), i.e., the measurement data set, on the graph is shifted to a new position i' from the position i. This means that the temporal axis of the measurement data is scaled (extended or shrunk) and offset.

In Step S12, the arithmetic processing unit 11 records the measurement data sets corrected in Step S11 in the recording unit 13, thereby completing a series of processes.

By way of the aforementioned processes, it is possible to normalize (correct the temporal axis of) the mobility measurement data, using the reference waveform data prepared beforehand, without the use of a marker substance. Therefore, an analytical target can be identified accurately, using the mobility normalized data recorded in Step S12.

As can be understood from the explanation above, the accuracy of normalization in the present invention depends upon the accuracy of the reference waveform data. When analyses containing markers are possible in, for example, some reference laboratories, reference waveform data can be prepared by normalizing the mobilities measured as in conventional manners, using the marker information.

On the other hand, in the case of an analytical method that cannot include a marker, the waveform data determined by self-organizing map (SOM) can be used as reference waveform data. Since SOM and the method of generating SOMs are well-known, a detailed explanation thereof is omitted; an example of an application of SOM to mobility measurement data is explained below. As described above, unit time sequence data for mobilities measured using chromatography, electrophoresis, or the like is targeted (in the case of differential coefficient data at changing peak points, the data is converted to unit time sequence data).

First, from a plurality of waveform data sets measured using an analytical process that cannot include a marker, representative waveform data sets are selected, and these waveform data sets are visually corrected to provide initial reference waveform data sets. Next, clustering is performed on these reference waveform data sets using SOM to extract typical waveform data sets. The resulting extracted waveform data sets are the reference waveform data for use in this embodiment.

Figure 6:
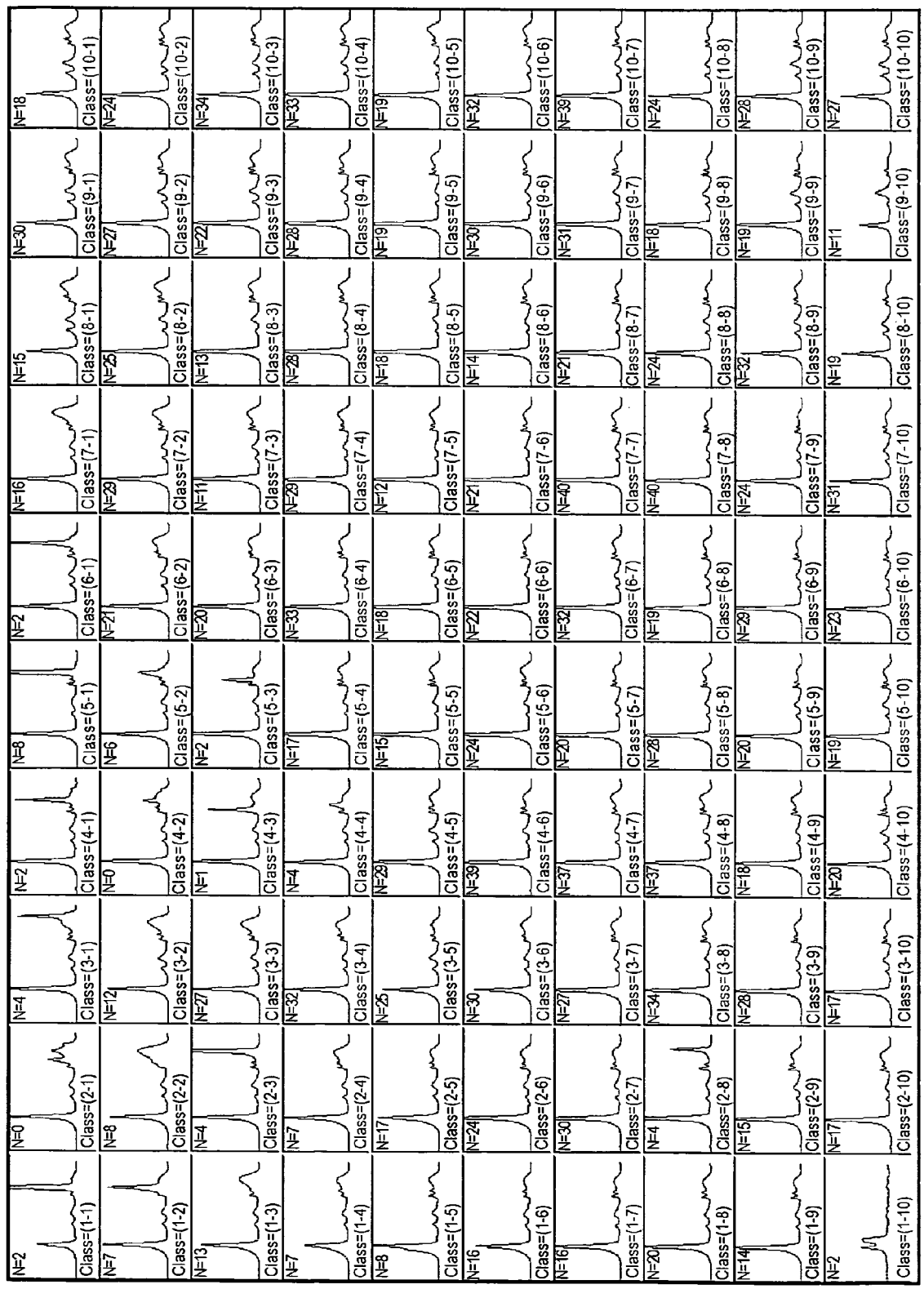
FIG. 6 is a diagram showing an example of an SOM determined using measurement data obtained by capillary electrophoresis.

If typical waveform data sets are not then extracted by clustering using SOM, the above-described correction procedure can be repeated until such data is extracted, so as to create reference waveform data with high accuracy. FIG. 6 shows an example of the reference waveform data measured using the measurement data obtained by capillary electrophoresis. In FIG. 6, the SOM consists of one-hundred reference waveform data sets. The correction accuracy can be enhanced by changing the number of reference waveform data sets according to the type of the waveform data for the target area.

The flowchart shown in FIG. 2 is merely an example, and does not limit the present invention. For example, although FIG. 2 illustrates a case in which DTW is applied to each reference waveform data set, and the results for all of the data sets are recorded in the recording unit, the present invention is not limited to this example: any other process may be used insofar as the WF for the most approximate reference waveform data set can be determined. Subsequent to the application of DTW on one reference waveform data set, the result of DTW may be compared with that of the previous other reference waveform data set, and only the WF of the smaller DTW distance (the coordinate data at the vertices) may be stored.

In addition, although Step S10 explained above involves linear approximation of the WF by using the medians of slopes and intercepts and excluding the outliers, the present invention is not limited to this example. For example, in the graph shown in FIG. 5, in which the slopes are sorted in order of increasing size, one value from the area with little fluctuation may be used, or the average value of the values in the area with little fluctuation may be used. This also applies to the intercepts.

Using reference waveform data of SOM generated as described above, it is possible to correct mobilities in an analytical process not using a marker at laboratories of general hospitals and the like. In this case, an SOM template (reference waveform data) with higher accuracy can be produced by accumulating many cases. Therefore, it is desirable that a newer SOM be provided as necessary to general hospitals or the like.

The mobility normalizing method according to the aforementioned embodiment can also be applied to a method for detecting a substance. Such a method for detecting a substance utilizing the normalizing method of the present invention can be implemented, for example, using the same normalizing apparatus 1 as that shown in FIG. 1. A method for protein detection utilizing the normalizing method of the present invention, which is implemented using an apparatus with the same configuration as that of the normalizing apparatus 1, is described below with reference to the same reference numerals as in FIG. 1.

First, a decision tree, which is a detection rule, is determined through learning that uses supervised data.

Specifically, the arithmetic processing unit 11 receives a mobility measured using an analyte obtained from each subject for an assembly of subjects including healthy individuals and patients suffering from a given disease, and records the mobility in the recording unit 13. The arithmetic processing unit 11 then reads the measurement data recorded in the recording unit 13 for correction using the normalizing method of the present invention. The arithmetic processing unit 11 subsequently reads information that represents whether each subject has a disease or not (hereinafter referred to as "supervised data"), which has previously been recorded in the recording unit 13, and performs learning, using the supervised data and the normalized measurement data, to determine a decision tree that classifies the protein related to the given disease. After the decision tree has thus been determined, the decision tree is applied, as a detection rule, to corrected data which are obtained by correcting mobility measurement data for general subjects (subjects other than those of the aforementioned assembly) using the normalizing method of the present invention, thereby determining whether each subject has a protein related to the given disease or not. Decision trees and the method for determining decision trees are known in public and therefore the explanation is omitted.

In addition, as will be described in the Examples below, the decision tree thus determined can be implemented as a computer program. It can further be implemented as computer data having the data structure that corresponds to the decision tree. When the decision tree is implemented as computer data, it may be executed by a computer program, using each data set included in the data structure as a detection parameter.

The mobility normalizing process or the protein detection process can also be offered as a service. For example, a server computer, which is similarly constructed as in FIG. 1 except that the measuring apparatus 2 is excluded, and which is connected to a communication network, is installed at a service provider facility. The service facility receives mobility measurement data from an external facility such as a general hospital, corrects the measurement data by executing the normalizing process of the present invention using the server computer, and provides the external facility, i.e., a client, with the corrected data. The service facility can also perform the protein detection process of the present invention using the corrected data, and provide the external facility, the client, with the results. At this time, the mobility measurement data can be supplied to the server computer, or the client can be provided with the data of the processing results, via the communication network or using a mobile recording medium such as a flexible disk, CD-ROM, USB memory, or the like.

Although protein detection is described above as one example, analytical targets are not limited thereto. Through the application of the present invention, the mobility of any substance capable of being analyzed based on its mobility can be accurately corrected, and hence the analytical target can be accurately detected. For example, by changing the detector of the measuring apparatus according to the analytical target, it is possible to acquire a waveform characteristic of each substance, and hence the waveform can be accurately corrected. For example, bacteria identification, determination of tolerance of antibiotics, etc., can also be performed accurately.

EXAMPLE 1

The features of the present invention will further be clarified with reference to the Examples shown below.

Figure 7:
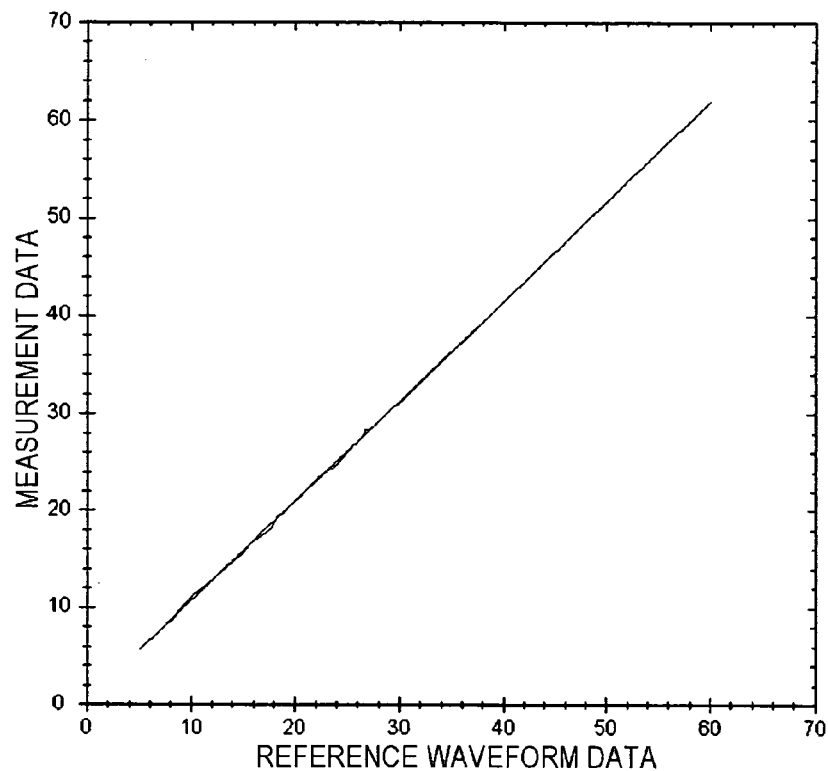
FIG. 7 is a graph of an example showing a WF determined by DTW in chromatography, and its approximate linear line.
Figure 8:
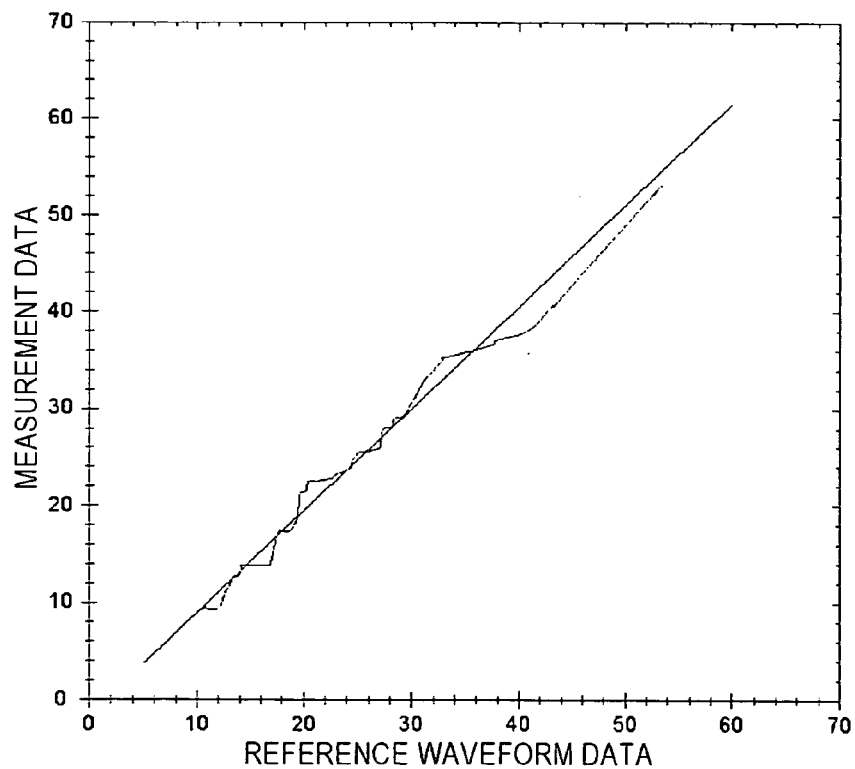
FIG. 8 is a graph of an example showing a WF determined by DTW in chromatography, and its approximate linear line.

FIG. 7 and FIG. 8 are graphs of examples, each showing a WF determined using DTW in chromatography and its approximate straight line. FIG. 7 presents the result in comparison with the most approximate waveform, using the reference waveform data of SOM shown in FIG. 6. Here, the WF is substantially a straight line. FIG. 8, on the other hand, presents a WF determined without using reference waveform data of SOM. Here, although the trend in mobility can be seen, the WF is less straight, so that if the mobility is corrected using the slope and intercept determined from this graph, there will be a large error. It can thus be seen that the use of reference waveform data determined by SOM enables mobility to be accurately corrected. Even in cases where the WF is distorted by abnormal peaks appearing at some portions of the mobility measurement waveform due to the presence of peculiar proteins or the like in the analyte, the mobility can be corrected by linear approximation.

Figure 9:
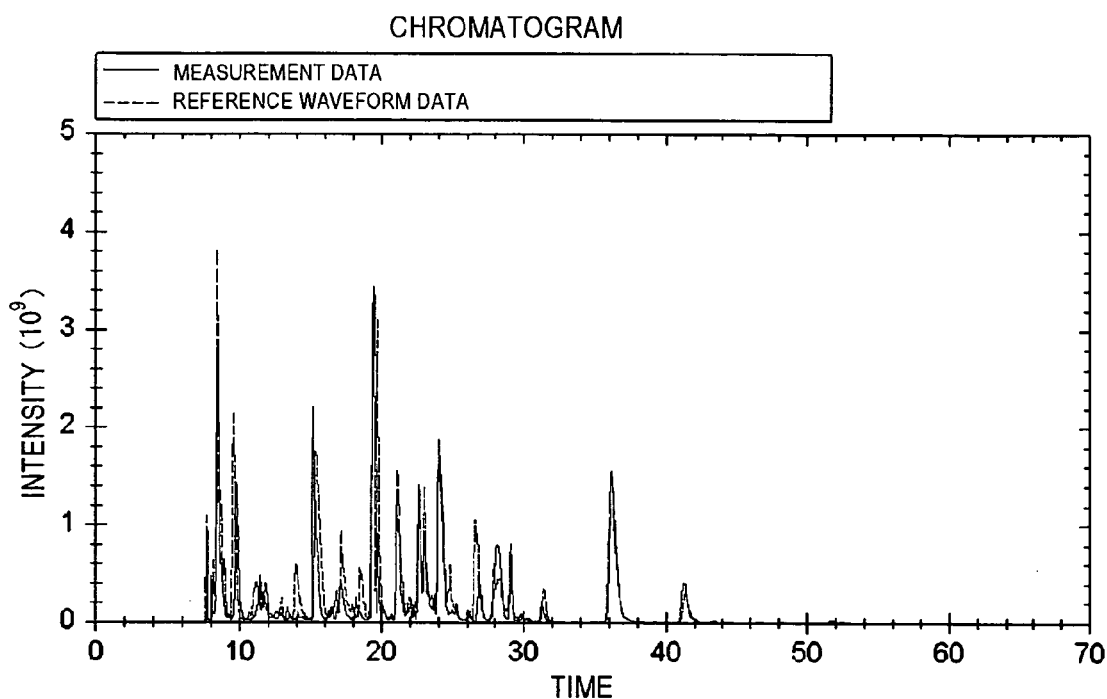
FIG. 9 is a graph showing an example of the results obtained by correcting a mobility measured by chromatography.

FIG. 9 is a graph showing an example of the results obtained by correcting a mobility as described above. FIG. 9 presents the reference waveform data and the results of corrected measurement data as overlapping with each other. It can be seen from FIG. 9 that the mobility has been accurately corrected by the normalizing method of the present invention.

EXAMPLE 2

An example of an application of the present invention to measurement data obtained by capillary electrophoresis is described. In this Example, a measuring apparatus, CZE 2000 manufactured by Beckman Coulter, Inc., was used, and uncorrected measurement data outputted from this apparatus was used. Measurements were conducted using dimethylformamide as a marker, followed by correction using the marker, and an SOM was yielded to determine the reference waveform data.

Figure 10:
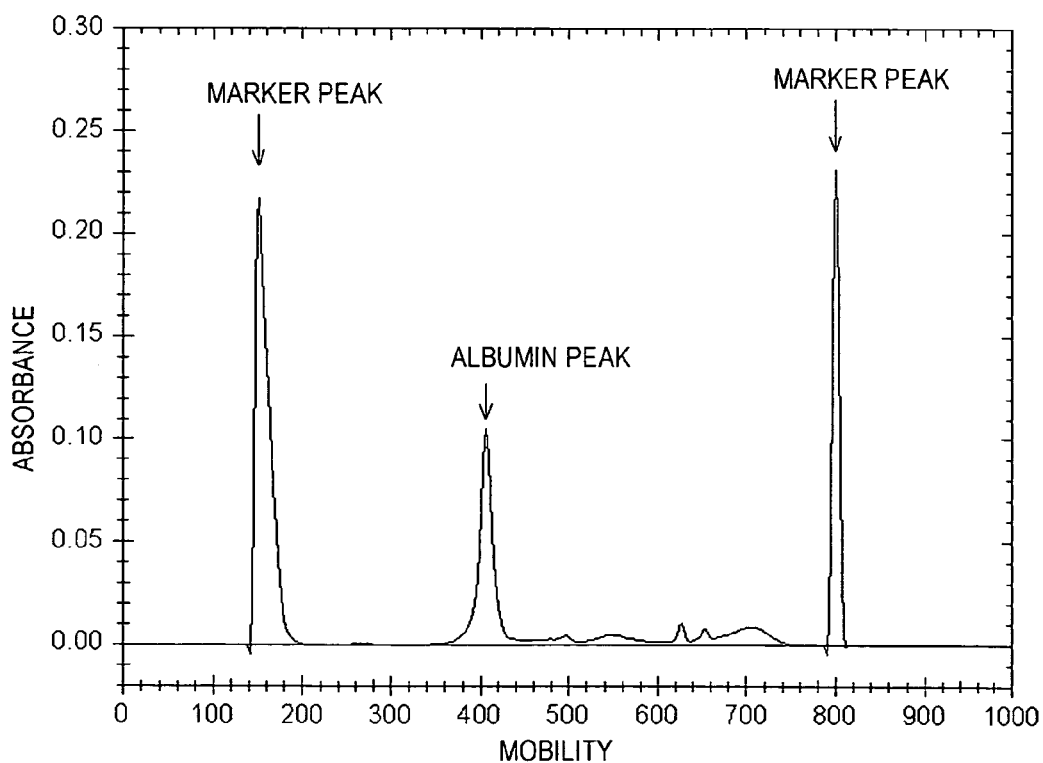
FIG. 10 is a graph showing an example of the results obtained by correcting measurement data obtained by capillary electrophoresis, using a marker.

FIG. 10 is a graph showing an example of measurement data corrected using a marker so that the mobility of albumin was 400 and the mobility of the marker (dimethylformamide) in the y-region was 800 (peaks of albumin and dimethylformamide are observed at mobility positions of 400 and 800, respectively). Since the peak of the marker on the left in FIG. 10 was unstable, it was not used as a reference for marker correction.

Figure 11:
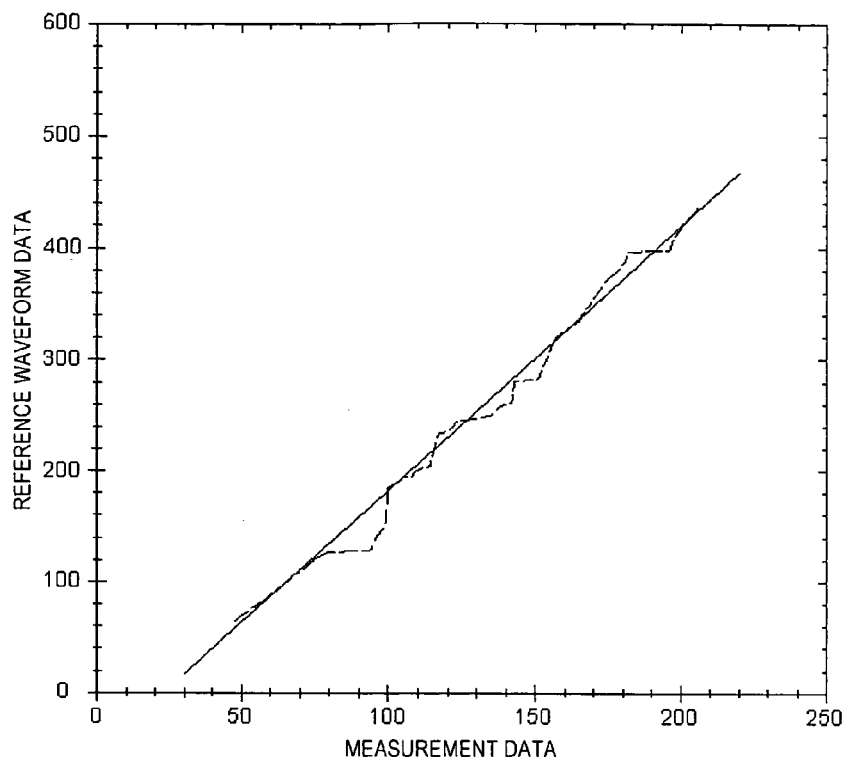
FIG. 11 is a graph showing measurement data without marker correction and a WF for the most approximate reference waveform data determined by DTW.

FIG. 11 is a graph showing given measurement data without marker correction and a WF for the most approximate reference waveform data determined using DTW. FIG. 11 depicts the approximate straight line of the WF as overlapping with the measurement data. The DTW distance was $4.81007 \times 10^2$; the slope $\alpha=2.371$ and the intercept $\beta=-54.529$.

Figure 12:
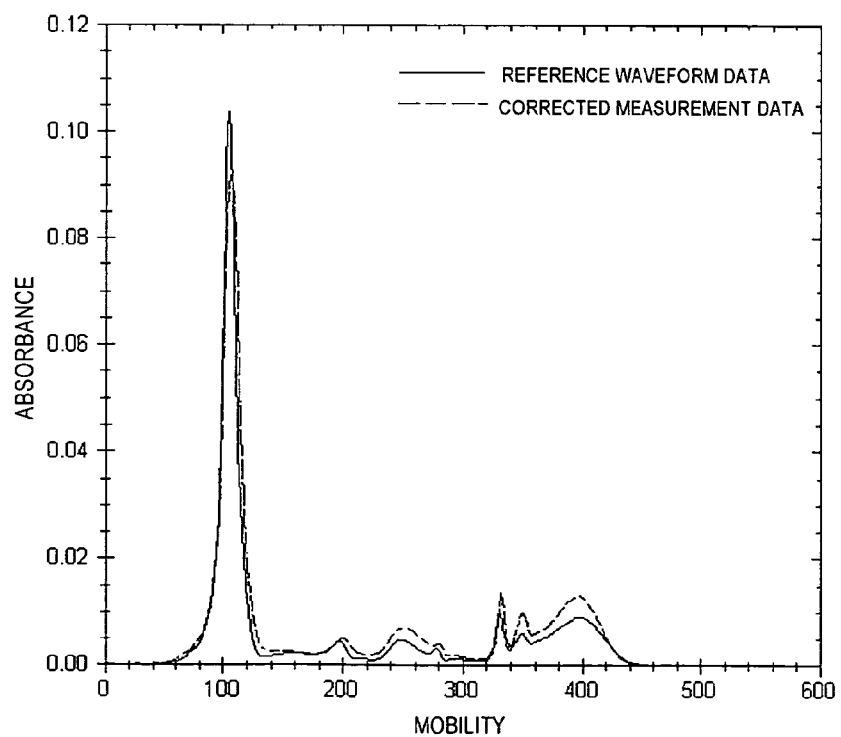
FIG. 12 is a graph showing the measurement data normalized by the normalizing method of the present invention, using the slope and intercept determined from the WF shown in FIG. 11, and the corresponding reference waveform data.

FIG. 12 is a graph showing the measurement data normalized by the normalizing method of the present invention (by the dashed line), using the slope $\alpha$ and intercept $\beta$ determined from the WF shown in FIG. 11. For reference, the reference waveform data (the waveform corrected using a marker) is shown by the solid line. Thus, using the normalizing method of the invention, it was possible to correct the mobility without marker correction. Note that the mobilities (horizontal axis) shown in FIG. 12 are values given by subtracting 300 from the mobilities shown in FIG. 10; for example, a mobility of 400 in FIG. 10 corresponds to a mobility of 100 in FIG. 12.

EXAMPLE 3

The accuracy of the normalizing method of the present invention is described. As in Example 2, the mobility of albumin was measured by capillary electrophoresis, using dimethylformamide as a marker, after which 2344 waveforms (measurement data) were sampled, and these measurement data sets were corrected with the marker to determine an SOM, thereby determining the reference waveform data. In addition, an analyte of M protein containing albumin was similarly measured, after which 14 waveforms (measurement data) were sampled, and each measurement data set was corrected using the normalizing method of the invention.

Albumin mobilities (at peak positions of mobility near 100) for the 2344 waveform data sets after the marker correction were statistically processed. As a result, the mean value (Mean) was 106.3, and the standard deviation (SD) was 1.01. On the other hand, albumin mobilities were statistically processed similarly for the 14 waveform data sets obtained by correcting the measurement data for the M protein-containing analyte using the normalizing method of the invention; as a result, the mean value (Mean) was 106.5, and the standard deviation (SD) was 1.40. It can therefore be seen that mobility can be corrected with equal accuracy to that of a correction method using a marker, or accuracy with only a slightly larger error.

In addition, mobilities of M protein (at peak positions of mobility near 360) were similarly statistically processed. As a result, the mean value (Mean) was 361.4, and the standard deviation (SD) was 1.39. For comparison, measurement data for an M protein-containing analyte (the waveform data obtained by measuring 14 times the same analyte sampled from a patient with myeloma having M protein; the data including variations in lots and analytical mechanisms was corrected with the marker, and the mobilities of M protein were statistically processed. As a result, with respect to the M protein mobilities, the mean value (Mean) was 361.6, and the standard deviation (SD) was 0.93. These results also demonstrate that the normalizing method of the invention provides equal accuracy to that of correction using a marker.

Figures 13, 14:
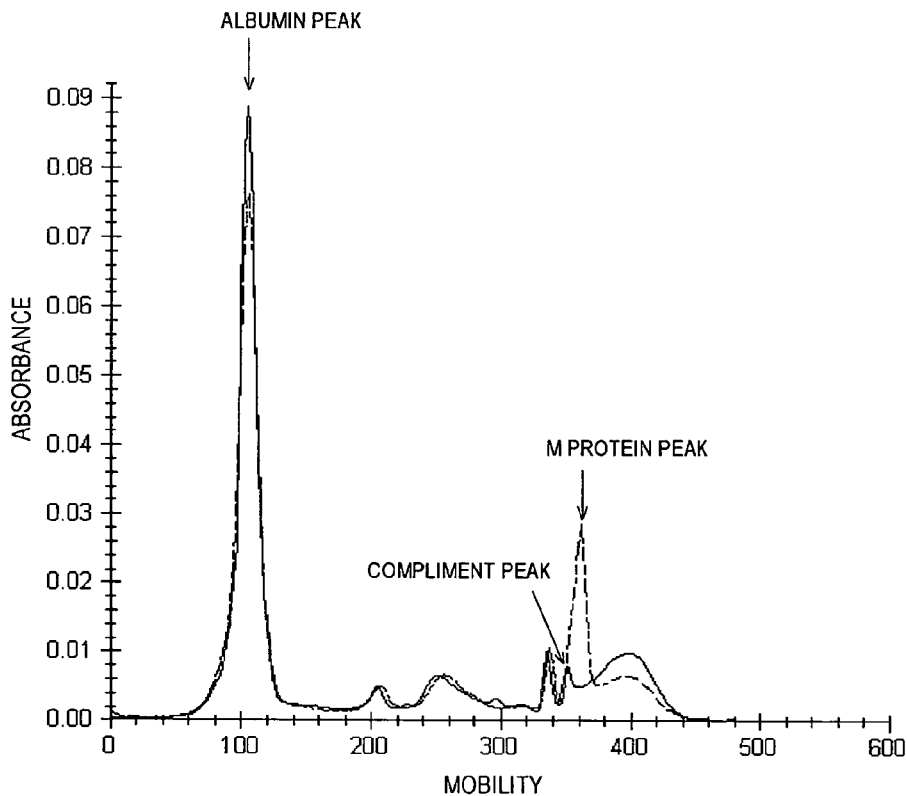
FIG. 13 is a graph showing corrected waveform data of M protein in capillary electrophoresis, and its reference waveform data.
FIG. 14 is a diagram showing an example of an M protein detection rule for use in the substance detection method according to the present invention.

FIG. 13 is a graph showing the reference waveform data used in the above-described accuracy test, and the corrected waveform data of M protein. The waveform indicated by the dashed line is one of the 14 waveforms after correcting the M protein measurement data using the normalizing method of the invention, and the waveform indicated by the solid line is a reference waveform most approximate to the waveform of the dashed line. The peaks near 100 (by the solid and dashed lines) represent the mobilities of albumin, and the peaks near 360 (by the dashed line) represent the mobilities of M protein. Cases of M protein are among cases of waveform peaks that are most likely be visually mistaken by the normal compliment due to overlap with the peak of the compliment (the portion of the solid line indicated by the arrow); however, it can be seen that, through the application of the normalizing method of the invention, the peak of M protein can be clearly separated from the peak of the compliment.

EXAMPLE 4

An example where the protein detection method, which is an application of the normalizing method of the invention, is applied to detecting M protein is described. In this Example, 608 medical examination analytes and 89 cases of M protein were used, and the decision tree for detecting M protein was determined in the manner as described above. As a result, the detection rule shown in FIG. 14, which is described in 20 lines, was determined. Here, reference waveform data was used which was determined by correcting the measurement data under the condition that the mobility of albumin was 400 and the mobility of the marker dimethylformamide in the γ region was 800, and by determining an SOM.

The detection rule shown in FIG. 14 has the structure of a decision tree. In FIG. 14, the numerical values at the left end in each line (for example, "779" in line 1) represent mobility; and the inequality sign (<or >) and the equal sign (=) represent the determination signs for specifying which of the right side and the left side is greater or smaller. The meanings of the determination signs are the same as those used in usual computer programming. The numerical value of the right side of each determination sign (for example, "0.00048" in line 1) represents absorbance. In addition, on the right of the colon (:) in each line is displayed the final detection result: Normal and Mpro denote healthy individuals and cases of M protein, respectively, and the numerical value within the parentheses denotes the number of the cases corresponding to Normal or Mpro. Hence, when the numerical values within parentheses for Normal and Mpro are summed, the resulting sums will become 608 and 89, respectively, which are the numbers of the cases used to determine the detection rule. As indicated by the oval, the detection rule was capable of detecting 64 cases of M protein without any error. Moreover, the detection rule was applied to about 8000 normalized measurement data sets. As a result, cases of M protein were detected at an error rate of 0%.

Note that the determination target of the determination equation in each line shown in FIG. 14, i.e., the mobility, and the determination signs (i.e., inequality sign and equal sign) hardly change as long as the mobility of albumin is 400 and the mobility of the marker, dimethylformamide, in the γ region is 800; however, the absorbances, which are the reference values for determination, can vary depending on the measurement data or learning, and are therefore not limited to the values shown in FIG. 14.

In addition, using 1161 medical examination analytes and 50 cases of M protein, the decision tree for detecting M protein was determined in the manner as described above. As a result, the detection rule shown in FIG. 15, which is described in 22 lines, was determined. FIG. 15 uses the same notation as that of FIG. 14 except that, of the numerical values within parentheses, those on the right of slashes (/) represent the numbers of cases in which cases of M protein were erroneously determined to be normal. Hence, when the numerical values within parentheses and the numerical values on the left of slashes for Normal are summed, and the numerical values within parentheses and the numerical values on the right of slashes for Mpro are summed, the resulting sums will be 1161 and 50, respectively, which are the numbers of the cases of data used in determining the detection rule. As in FIG. 14, the mobilities are the values determined by correcting the measurement data under the condition that the mobility of albumin is 400 and the mobility of the marker, dimethylformamide, in the y region is 800. Note that the absorbances are relative values, and thus cannot be directly compared with the values shown in FIG. 14. A decision tree with an error rate of 1.0% (=12/1161) was derived from this detection rule. The rule of this decision tree was tested by mixing medical examination analytes with cases of M protein; as a result, both the sensitivity and specificity were 100%, thus yielding favorable results. On the other hand, when the rule was applied to a general diagnosis, the sensitivity was 76% and the specificity was 100%. The term "sensitivity" referred to herein means a value calculated by the number of true positive cases/(the number of true positive cases+the number of false negative cases)×100(%), i.e., the detection percentage for M protein positive that is detectable using this detection rule. The specificity means a value calculated by the number of true negative cases/(the number of false positive cases+true negative)×100 (%), i.e., the negative percentage in the M protein negative group.

For comparison, FIG. 16 shows a decision tree determined using the prior art methods described in Patent Documents 1 and 3. Specifically, each of the normalized waveform data sets for 608 medical examination analytes and 89 cases of M protein, which are the same as used above, was differentiated, after which the waveform position x, height y, left half-width lhw, and right half-width rhw were calculated as feature amounts of each waveform, and learning was performed using these feature amounts. Although FIG. 16 uses the same notation as that of FIG. 14, it is different from FIG. 14 in that the determination target is not mobility but the waveform position x, height y, left half-width lhw, and right half-width rhw; and in that the number of cases of errors is shown on the right of slashes (/) within parentheses. Although only a part of the detection rule is shown in FIG. 16, the detection rule consists of a total of 347 lines of determination equations and is very complicated. In addition, from the determination results in line 6 (correct: 840 cases, error: 35 cases), for example, it is seen that the detection accuracy is also poor. Accordingly, the method of detecting a substance, and in particular, protein, which is an application of the normalizing method of the present invention, proved to be very effective.

INDUSTRIAL APPLICABILITY

The mobility normalizing apparatus, normalizing method, normalizing program, and self-organizing map according to the present invention are capable of normalizing mobilities for analyzing waveform information obtained by electrophoresis in clinical examinations or gene analyses. In addition, the detection method, detection program, detection rule creating method, and data structure according to the present invention can be used in detecting a substance based on its mobility in clinical examinations or gene analyses.

The invention claimed is:

1. A mobility normalizing apparatus comprising:
   a recording unit containing a plurality of reference waveform data sets; and
   a processing unit; wherein the processing unit
      defines the measurement data as data to be corrected, when externally acquired mobility measurement data is unit time sequence data;
      interpolates a plurality of two-dimensional data sets to create the data to be corrected, the data to be corrected being unit time sequence data, when externally acquired mobility measurement data is the plurality of two-dimensional data sets associated with time information and measured values;
      reads the plurality of reference waveform data sets from the recording unit, and determines a plurality of warping functions converting the data to be corrected to the respective plurality of reference waveform data sets, and a Dynamic Time Warping (DTW) distance associated with each warping function;
      evaluates a minimum value of the plurality of DTW distances, and determines the warping function associated with the determined minimum DTW distance;
      determines a slope and an intercept of a straight line approximating the determined warping function; and
      corrects the data to be corrected using a linear function specified by the slope and the intercept and obtains a normalized data; and wherein
   the mobility measurement data is obtained from mobility measurement of an analytical target without mixing a marker substance into a sample.

2. The mobility normalizing apparatus according to claim 1, wherein the processing unit calculates a slope between given vertices for each determined warping function, excludes slopes included in predetermined areas at both ends when the plurality of slopes between vertices are arranged in order of increasing size, and determines the slope of the straight line approximating the warping function based on the slopes between vertices which are not excluded.

3. The mobility normalizing apparatus according to claim 2, wherein the processing unit determines a median of the plurality of slopes between vertices as the slope of the straight line approximating the warping function.

4. The mobility normalizing apparatus according to claim 1, wherein the plurality of reference waveform data sets are data obtained by correcting mobility measurement data for an analyte containing a marker substance, using the mobility of the marker substance.

5. The mobility normalizing apparatus according to claim 1, wherein the plurality of reference waveform data sets are data forming a self-organizing map created using a plurality of mobility measurement data sets.

6. A mobility normalizing method comprising:
   a first step of determining, in a processor device, a plurality of warping functions converting data to be corrected, which is unit time sequence data obtained by measuring mobility of an analytical target without mixing a marker substance into a sample, to respective plurality of given reference waveform data sets, and a Dynamic Time Warping (DTW) distance associated with each warping function;
   a second step of evaluating, in the processor device, a minimum value of the plurality of DTW distances, and determining the warping function associated with the determined minimum DTW distance;
   a third step of determining, in the processor device, a slope and an intercept of a straight line approximating the determined warping function; and
   a fourth step of correcting, in the processor device, the data to be corrected using a linear function specified by the slope and the intercept and obtaining a normalized data.

7. The mobility normalizing method according to claim 6, wherein the data obtained by measuring mobility is a plurality of two-dimensional data sets associated with time information and measured values; and wherein
   the data to be corrected is unit time sequence data created by interpolating the plurality of two-dimensional data sets.

8. The mobility normalizing method according to claim 6, wherein the third step comprises:
   a fifth step of calculating, in the processor device, a slope between given vertices for each warping function determined in the second step; and
   a sixth step of excluding, in the processor device, slopes included in predetermined areas at both ends when the plurality of slopes between vertices are arranged in order of increasing size, and determining the slope of the straight line approximating the warping function based on the slopes between vertices which are not excluded.

9. The mobility normalizing method according to claim 8, wherein the sixth step is a step of determining, in the processor device, a median of the plurality of slopes between vertices as the slope of the straight line approximating the warping function.

10. The mobility normalizing method according to claim 6, wherein the plurality of given reference waveform data sets are data obtained by correcting mobility measurement data for an analyte containing a marker substance, using the mobility of the marker substance.

11. The mobility normalizing method according to claim 6, wherein the plurality of given reference waveform data sets are data forming a self-organizing map created using a plurality of mobility measurement data sets.

12. A non-transitory computer-readable recording medium containing instructions for a mobility normalizing program stored therein, wherein a processor device comprises a recording unit containing a plurality of reference waveform data sets, and a processing unit; the instructions for causing the processing unit to perform the steps of:
   determining a plurality of warping functions converting data to be corrected, which is unit time sequence data obtained by measuring mobility of an analytical target without mixing a marker substance into a sample, to respective plurality of reference waveform data sets, and a Dynamic Time Warping (DTW) distance associated with each warping function;

evaluating a minimum value of the plurality of DTW distances, and determining the warping function associated with the determined minimum DTW distance;
determining a slope and an intercept of a straight line approximating the determined warping function; and
correcting the data to be corrected using a linear function specified by the slope and the intercept and obtaining a normalized data.

13. A non-transitory computer-readable recording medium containing instructions for a self-organizing map stored therein, the instructions for performing, on a processor device:
  using the self-organizing map as the reference waveform data in
    a first step of determining, in a processor device, a plurality of warping functions converting data to be corrected, which is unit time sequence data obtained by measuring mobility of an analytical target without mixing a marker substance into a sample, to respective plurality of given reference waveform data sets, and a Dynamic Time Warping (DTW) distance associated with each warping function;
    a second step of evaluating, in the processor device, a minimum value of the plurality of DTW distances, and determining the warping function associated with the determined minimum DTW distance;
    a third step of determining, in the processor device, a slope and an intercept of a straight line approximating the determined warping function; and
    a fourth step of correcting, in the processor device, the data to be corrected using a linear function specified by the slope and the intercept and obtaining a normalized data,
  wherein the self-organizing map comprises typical waveform data sets; and
  creating the self-organizing map by a learning process executed by the processor device till the typical waveform data sets are extracted by performing self-organizing map clustering of waveform data obtained by visually correcting data to be corrected, which is unit time sequence data obtained by measuring mobility of an analyte not containing a marker substance, or by performing self-organizing map clustering of waveform data obtained by correcting data to be corrected, which is unit time sequence data obtained by measuring mobility of an analyte containing the marker substance, based on the mobility of the marker substance.

14. A processor-implemented substance detection method comprising:
  using, in a processor device, a decision tree determined as a detection rule by learning that uses supervised data;
  determining, in the processor device, the decision tree by learning that performs:
    obtaining normalized data by correcting a plurality of mobility measurement data sets for a plurality of analytes not containing a marker substance, using
      a first step of determining the processor device, a plurality of functions converting data to be corrected, which time sequence data obtained by measuring mobility of an analytical target without mixing a marker substance into a sample, to respective plurality of given reference waveform data sets, and a Dynamic Time Warping (DTW) distance associated with each warping function;
      a second step of evaluating, in the processor device, a minimum vale of the plurality of DTW distances, and determining the warping function associated with the determined minimum DTW distance;
      a third step of determining, in the processor device, a slope and an intercept of a straight e approximating the determined warping function; and
      a fourth step of correcting, in the processor device, the data to be corrected using a linear function specified b the slope and the intercept and obtaining a normalized data;
  wherein the supervised data includes information representing the presence or absence of a given substance, which is associated with each measurement data set.

15. A non-transitory computer-readable recording medium containing instructions of a substance detection program stored therein for causing a processor device to perform a function of detecting a substance, the instructions for implementing the steps of:
  using a decision tree determined as a detection rule by learning that uses supervised data;
  determining the decision tree by learning that performs:
    obtaining normalized data by correcting a plurality of mobility measurement data sets for a plurality of analytes not containing a marker substance, using
      a first step of determining a plurality of warping functions converting data to be corrected, which is unit time sequence data obtained by measuring mobility of an analytical target without mixing a marker substance into a sample to respective plurality of given reference waveform data sets, and a Dynamic Time Warping (DIV) distance associated with each warping function;
      a second step of evaluating a minimum value of the plurality of DTW distances, and determining the warping function associated with the determined minimum DTW distance;
      a third step of determining a slope and an intercept of a straight line approximating the determined warping function; and
      a fourth step of correcting the data to be corrected using a linear function specified by the slope and the intercept and obtaining a normalized data;
  wherein the supervised data includes information representing the presence or absence of a given substance, which is associated with each measurement data set.

16. A processor device-implemented method for creating a detection rule for use in detecting a substance, the method comprising:
  a first step of using a processor device to correct a plurality of mobility measurement data sets for a plurality of analytes not containing a marker substance, using the following steps to create normalized data:
    a step of determining, in the processor device, a plurality of warping functions converting data to be corrected, which is unit time sequence data obtained by measuring mobility of an analytical target without mixing a marker substance into a sample to respective plurality of given reference waveform data sets, and a Dynamic Time Warping (DTW) distance associated with each warping function;
    a step of evaluating, in the processor device, a minimum value of the plurality of DTW distances, and determining the warping function associated with the determined minimum DTW distance;
    a step of determining, in the processor device, a slope and an intercept of a straight tine approximating the determined warping function; and a step of correcting, in the processor device the data to be corrected using a linear function specified by the slope and the intercept and obtaining a normalized data; and a second step of determining, in the processor device, a decision tree as a detection rule by learning, using supervised data including information representing the presence or absence of a given substance, which is associated with each measurement data set, and the normalized data.

17. A non-transitory computer-readable recording medium containing instructions of a data structure for being used as a substance detection rule, the instructions when executed on a processor device implement the steps of:

representing the data structure as a decision tree determined by learning that performs:

obtaining normalized data by correcting a plurality of mobility measurement data sets for a plurality of analytes not containing a marker substance, using a first step of determining a plurality of Tarping functions converting data to be corrected, which is unit time sequence data obtained by measuring mobility of an analytical target without mixing a marker substance into a sample, to respective plurality of given reference waveform data sets, and a Dynamic Time Warping (DTW distance associated with each warping function;

a second step of evaluating a minimum value of the plurality of DTW distances, and determining the warping function associated with the determined minimum DTNAT distance;

a third step of determining a slope and an intercept of a straight line approximating the determined warping function; and a fourth step of correcting the data to be corrected using a linear function specified by the slope and the intercept and obtaining a normalized data;

detecting a presence or absence of a given substance based on supervised data, the supervised data including information representing the presence or absence of a given substance, which is associated with each measurement data set.

* * * * *